United States Patent
Donhowe et al.

(10) Patent No.: US 12,369,780 B2
(45) Date of Patent: Jul. 29, 2025

(54) METHOD AND SYSTEM FOR STEERABLE MEDICAL DEVICE PATH DEFINITION AND FOLLOWING DURING INSERTION AND RETRACTION

(71) Applicant: Intuitive Surgical Operations, Inc., Sunnyvale, CA (US)

(72) Inventors: Caitlin Q. Donhowe, Mountain View, CA (US); Amir Belson, Los Altos, CA (US); Kristoffer J. Donhowe, Sunnyvale, CA (US); Kenneth R. Krieg, Fremont, CA (US); Eric Storne, Menlo Park, CA (US); Thomas J. Yorkey, San Ramon, CA (US); Jun Zhang, Dublin, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 964 days.

(21) Appl. No.: 16/999,592

(22) Filed: Aug. 21, 2020

(65) Prior Publication Data

US 2021/0038055 A1    Feb. 11, 2021

Related U.S. Application Data

(63) Continuation of application No. 16/048,438, filed on Jul. 30, 2018, now abandoned, which is a
(Continued)

(51) Int. Cl.
*A61B 1/005* (2006.01)
*A61B 1/00* (2006.01)
(Continued)

(52) U.S. Cl.
CPC ...... *A61B 1/0051* (2013.01); *A61B 1/000096* (2022.02); *A61B 1/00148* (2022.02);
(Continued)

(58) Field of Classification Search
CPC ........................................ A61B 1/00147–0016
See application file for complete search history.

(56) References Cited

U.S. PATENT DOCUMENTS 6,468,203 B2   10/2002   Belson
6,610,007 B2    8/2003   Belson et al.
(Continued)

FOREIGN PATENT DOCUMENTS

WO   WO-2009097461 A1   8/2009

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Alexandra L Newton
(74) *Attorney, Agent, or Firm* — Haynes & Boone, LLP.

(57) ABSTRACT

A method may comprise storing a first waypoint corresponding to a first position of a tip of a steerable medical device including an articulatable segment. The controller may perform a motion pause check operation to determine that an insertion motion of the articulatable segment into a patient anatomy has been paused, while the tip is at a second position. The controller may determine that the articulatable segment has resumed the insertion motion into the patient anatomy. After determining that the articulatable segment has resumed the insertion motion, a second waypoint corresponding to the second position of the tip of the steerable medical device, may be stored. A boundary region may be defined to form a three-dimensional volume enclosing the
(Continued)

positions of the stored waypoints. The articulatable segment may be constrained to remain within the boundary region as the articulatable segment is inserted in the patient anatomy.

18 Claims, 5 Drawing Sheets

Related U.S. Application Data continuation of application No. 12/613,739, filed on Nov. 6, 2009, now abandoned.

(60) Provisional application No. 61/113,534, filed on Nov. 11, 2008.

(51) Int. Cl.
*A61B 17/00* (2006.01)
*A61B 34/10* (2016.01)
*A61B 90/00* (2016.01)

(52) U.S. Cl.
CPC ... *A61B 2017/003* (2013.01); *A61B 2034/107* (2016.02); *A61B 90/03* (2016.02)

(56) References Cited

U.S. PATENT DOCUMENTS

| | | |
|---|---|---|
| 8,568,302 B2 | 10/2013 | Donhowe et al. |
| 9,517,000 B2 | 12/2016 | Donhowe et al. |
| 9,913,572 B2 | 3/2018 | Donhowe et al. |
| 2003/0191367 A1 | 10/2003 | Belson et al. |
| 2004/0176683 A1 | 9/2004 | Whitin et al. |
| 2004/0249269 A1 | 12/2004 | Shiono et al. |
| 2006/0258912 A1* | 11/2006 | Belson .................. A61B 1/009 600/152 |
| 2007/0135803 A1 | 6/2007 | Belson |
| 2007/0144298 A1* | 6/2007 | Miller .................. B25J 9/1676 74/490.01 |
| 2007/0197896 A1 | 8/2007 | Moll et al. |
| 2007/0249901 A1 | 10/2007 | Ohline et al. |
| 2007/0270650 A1 | 11/2007 | Eno et al. |
| 2008/0234700 A1 | 9/2008 | Trovato et al. |
| 2008/0287963 A1 | 11/2008 | Rogers et al. |
| 2009/0099420 A1 | 4/2009 | Woodley et al. |
| 2009/0137952 A1 | 5/2009 | Ramamurthy et al. |
| 2009/0171271 A1* | 7/2009 | Webster ............. A61B 17/3421 604/95.01 |
| 2009/0216083 A1 | 8/2009 | Durant et al. |
| 2010/0121145 A1 | 5/2010 | Donhowe |
| 2010/0121148 A1 | 5/2010 | Donhowe et al. |
| 2018/0333039 A1 | 11/2018 | Donhowe et al. |

\* cited by examiner

METHOD AND SYSTEM FOR STEERABLE MEDICAL DEVICE PATH DEFINITION AND FOLLOWING DURING INSERTION AND RETRACTION

RELATED APPLICATION

The present application is a continuation of U.S. patent application Ser. No. 16/048,438, filed Jul. 30, 2018, which is a continuation of U.S. patent application Ser. No. 12/613,739 (filed Nov. 6, 2009), which claims the benefit of the filing date of U.S. Provisional Patent Application No. 61/113,534 (filed Nov. 11, 2008) all of which are hereby incorporated by reference herein in their entirety.

BACKGROUND

Field of Invention

Aspects of this invention are related to medical device path planning, and more particularly are related to path planning for an articulatable multi-segment medical device.

Related Art

An endoscope is a medical device for visualizing the interior of a patient's body. Endoscopes have been used for a variety of medical diagnostic procedures and for a variety of medical interventional procedures.

Many different types of endoscopes are known. For example, one steerable endoscope has an elongated body with a steerable distal portion and an automatically controlled proximal portion. Such an endoscope is described in U.S. Pat. No. 6,468,203 B2, entitled "Steerable Endoscope and Improved Method of Insertion," of Amir Belson issued on Oct. 22, 2002, which is incorporated herein by reference in its entirety.

In general, conventional medical device path-planning is performed using medical imaging data usually CAT, X-ray, MRI, PET of fluoroscopy imaging data. Path-planning is considered in U.S. Pat. No. 5,611,025, entitled "Virtual internal cavity inspection system," issued Mar. 11, 1997; U.S. Pat. No. 7,167,180, entitled "Automatic path planning system and method," issued Jan. 23, 2007; U.S. Pat. No. 6,380,958, entitled "Medical-technical System," issued Apr. 30, 2002; U.S. Patent Application Publication No. US 2008/0091340 A1 (filed Dec. 26, 2004, disclosing "Targeted Marching"); and U.S. Patent Application Publication No. US 2003/0109780 A1 (filed Jun. 6, 2002, disclosing "Methods and Apparatus for Surgical Planning").

SUMMARY

Unlike prior art methods that required path planning prior to use of a steerable medical device, waypoints of a steerable medical device are stored as the device is moved within a patient. The stored waypoints are an ordered sequence of locations. The ordered sequence of locations defines a safe path within the patient for moving an articulatable portion of the steerable medical device.

Thus, the articulatable portion of the steerable medical device is constrained to follow the safe path as the articulatable portion moves within the patient or as the device is inserted into the patient. In one aspect, the articulatable portion of the steerable medical device is constrained to remain within a boundary region enclosing the safe path.

In one embodiment, the articulatable portion of the steerable medical device includes a segment of the steerable medical device. The segment, in turn, includes a plurality of links.

In another aspect, the boundary region is a tube having a cross-section. Examples of cross-sections include, but are not limited to, a circular cross-section, an oblate cross-section, and a rectangular cross cross-section.

In still yet another aspect, constraining the articulatable portion of the steerable medical device to remain within a boundary region enclosing the safe path includes generating position and orientation data for each of the plurality of segments. This process uses the ordered sequence of locations and a kinematic model of the plurality of segments of the steerable medical device.

The process of generating position and orientation data for each of the plurality of segments includes minimizing a cost function. In one aspect, minimizing a cost function further includes minimizing the sum of the absolute values of relative joint angles, with an additional constraint that link positions must remain within some distance $\Delta$ of the safe path formed by the waypoints.

An apparatus includes a steerable medical device having an articulatable portion. The articulatable portion includes at least one articulatable segment. The apparatus also includes a controller, coupled to the steerable medical device. The controller includes a processor, and a medical device controller coupled to the processor and to the steerable medical device. The processor stores in the memory an ordered sequence of locations of waypoints. The processor also analyzes the ordered sequence of locations and outputs to the medical device controller at least one command to constrain the articulatable portion within a boundary region enclosing a safe path defined by the ordered sequence of location.

Figure 1:
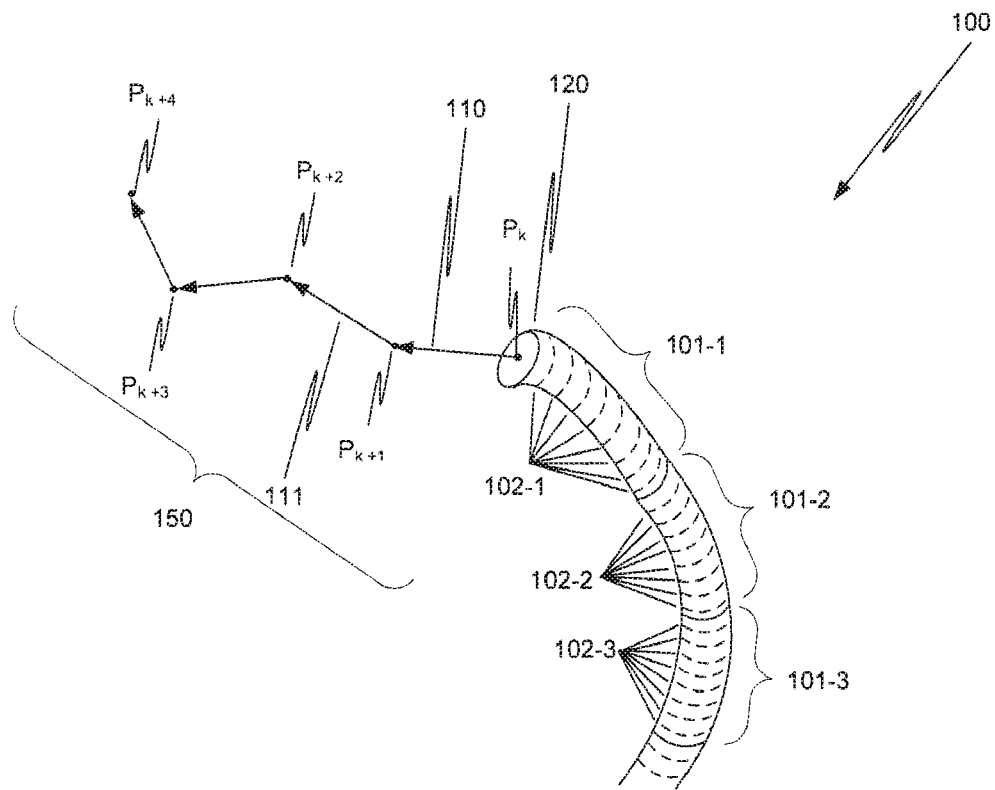
FIG. 1 is a diagrammatic view of a steerable medical device including an articulatable portion, and a safe path.

In the drawings, the first digit of a figure number indicates the figure in which the element with that figure number first appeared.

DETAILED DESCRIPTION

In one aspect, a steerable medical device 100 (FIG. 1), sometimes referred to as medical device 100, includes a plurality of segments 101-1, 101-2, 101-3 . . . . In the embodiment of FIG. 1, at least three segments 101-1, 101-2, 101-3 include a plurality of movable links 102-1, 102-2 and 102-3, respectively. In one aspect, a tip of steerable medical device 100 is at distal end 120 and typically includes at least a camera.

The use of a steerable medical device with at least three segments each having a plurality of movable links is illustrative only and in not intended to be limiting. In view of this disclosure, a steerable medical device may include from at least one segment having a plurality of links to a number of segments with movable links needed to provide the required functionality for the steerable medical device.

An example of a steerable medical device 100 is a steerable endoscope. In the following description, steerable medical device 100 is referred to as steerable endoscope 100. The use of steerable endoscope 100 as an example of a steerable medical device is illustrative only and is not intended to be limiting to this specific steerable medical device.

The plurality of movable links in a segment allows that segment to be articulated as steerable endoscope 100 moves into and out of a patient. Thus, such segments are referred to as articulatable segments.

In one aspect, an operator manipulates a direction controller 245 (FIG. 2) to move the tip of steerable endoscope 100 in a particular direction within the patient. In response to commands from a processor in processor module 250, as described more completely below, and a signal from direction controller 245, an endoscope controller 240 (FIG. 2) for steerable endoscope 100 configures each of the links so that each segment is constrained to move along, e.g., to follow, a known safe path 150 (FIG. 1) that is defined, in one aspect, by movement of the tip of endoscope 100.

In one embodiment, as the operator steers the tip of steerable endoscope 100 through the patient, a safe path is generated. More specifically, as the operator inserts steerable endoscope 100 into a patient and moves steerable endoscope 100 towards a desired location, an ordered sequence of locations $\{P_k, P_{k+1}, P_{k+2}, P_{k+3}, P_{k+4}\}$ (FIG. 1) of the tip of endoscope 100 are recorded in a memory 230 (FIG. 2) as waypoint data 231, in this example.

The ordered sequence of locations $\{P_k, P_{k+1}, P_{k+2}, P_{k+3}, P_{k+4}\}$ (FIG. 1) represent the motion of the tip of steerable endoscope 100 through the patient. Thus, the ordered sequence of locations $\{P_k, P_{k+1}, P_{k+2}, P_{k+3}, P_{k+4}\}$ represent a safe path 150, which has been chosen by the operator, for steerable endoscope 100 to follow as steerable endoscope 100 is inserted into and withdrawn from the patient.

Using the tip movement to generate an ordered sequence of locations that define safe path 150 is illustrative only and is not intended to be limiting. Alternatively, steerable endoscope 100 could be inserted in a passive state, and then all the inserted articulatable segments activated at one. The positions of the links in the articulatable segments at the time of activation provide an ordered sequence of locations that define safe path 150 for additional insertion and for retraction of steerable endoscope 100.

In one aspect, as described more completely below, all trailing segments 101-1, 101-2, 101-03 . . . of steerable endoscope 100 are constrained to follow safe path 150 that is defined by ordered sequence of locations $\{P_k, P_{k+1}, P_{k+2}, P_{k+3}, P_{k+4}\}$. However, trailing segments 101-1, 101-2, 101-03 . . . may not follow safe path 150 exactly. In one aspect, the operator can define a boundary region around safe path 150. The boundary region (See FIGS. 3A to 3C) is a volume inside which steerable endoscope 100 can move safely. In one aspect, all trailing segments 101-1, 101-2, 101-03 . . . are constrained to remain within this boundary region as steerable endoscope 100 moves into the patient.

Also, in another aspect, as medical device 100 is withdrawn from the patient, articulatable segments 101-1, 101-2, 101-03 . . . are constrained to remain within this boundary region. Hence, unlike prior art techniques that required advance planning, a safe route for medical device 100 into and out of a patient is generated based on waypoint data 231 recorded as steerable endoscope 100 moves into the patient.

When segment 101-1 is considered a trailing segment, as just described, segment 101-1 is controlled in the same way as the other trailing articulatable segments. However, in another insertion mode, segment 101-1 remains directly controlled by the operator and does not change shape with insertion. In this insertion mode, segment 101-1 would not be considered a trailing segment.

Figure 3A:
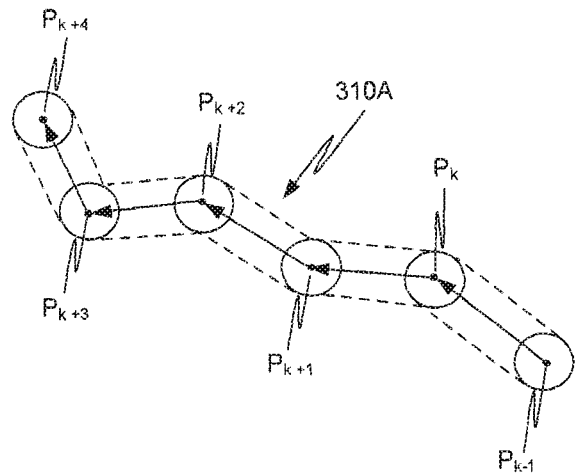
FIGS. 3A to 3C are diagrammatic views of boundary regions enclosing a safe path.
Figure 3B:
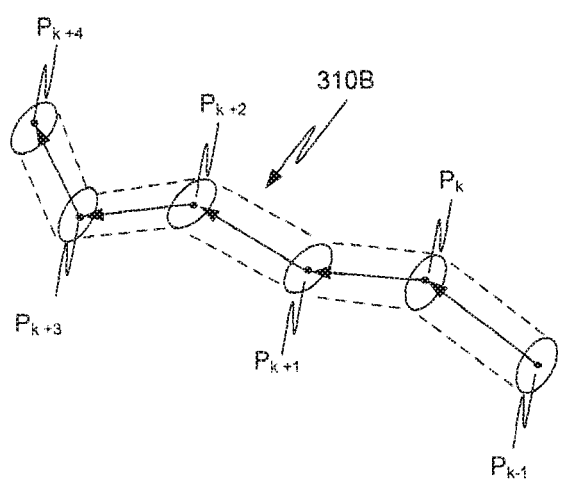
Figure 3C:
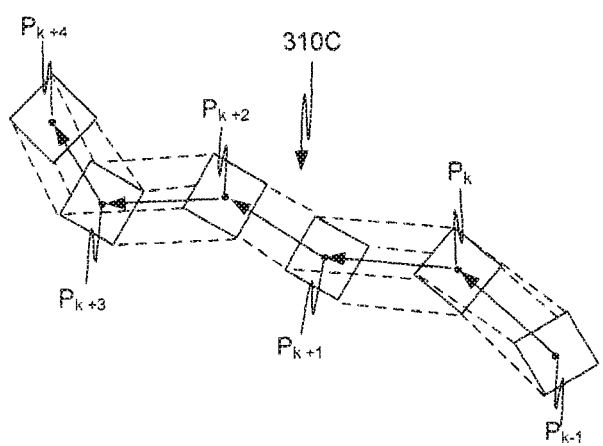

FIGS. 3A to 3C are illustrations of boundary regions 310A to 310C, with different cross-sectional shapes, for safe path 150 defined by ordered sequence of locations $\{P_k, P_{k+1}, P_{k+2}, P_{k+3}, P_{k+4}\}$. In FIG. 3A, boundary region 310A has a circular cross-section. In FIG. 3B, boundary region 310B has an oblate cross-section. In FIG. 3C, boundary region 310C has a rectangular cross-section, and in particular, a specific instance of a rectangular cross-section, a square cross-section.

In one aspect, each location $P_k$ is a point in space $(x_k, y_k, z_k)$ relative to a fixed reference frame. Thus, each of boundary regions 310A, 310B, 310C defines a three-dimensional volume enclosing safe path 150. This volume is referred to as a tube having a cross section to convey the three-dimensional characteristics of the volume. Tube, as used here, is not a physical tube inserted in the patient to define the volume.

The particular cross-sectional shapes of the boundary regions illustrated in FIGS. 3A to 3C are illustrative only and are not intended to be limiting. In view of this disclosure, for a particular medical procedure and steerable medical device, an appropriately shaped boundary region or regions can be selected.

It is not necessary that the boundary region have the same cross-sectional shape over the entire extent of the safe path. For example, a first portion of a boundary region could have a first cross-sectional shape, and a second portion of the boundary region could have a second cross-sectional shape that is different from the first cross-sectional shape.

Figure 4:
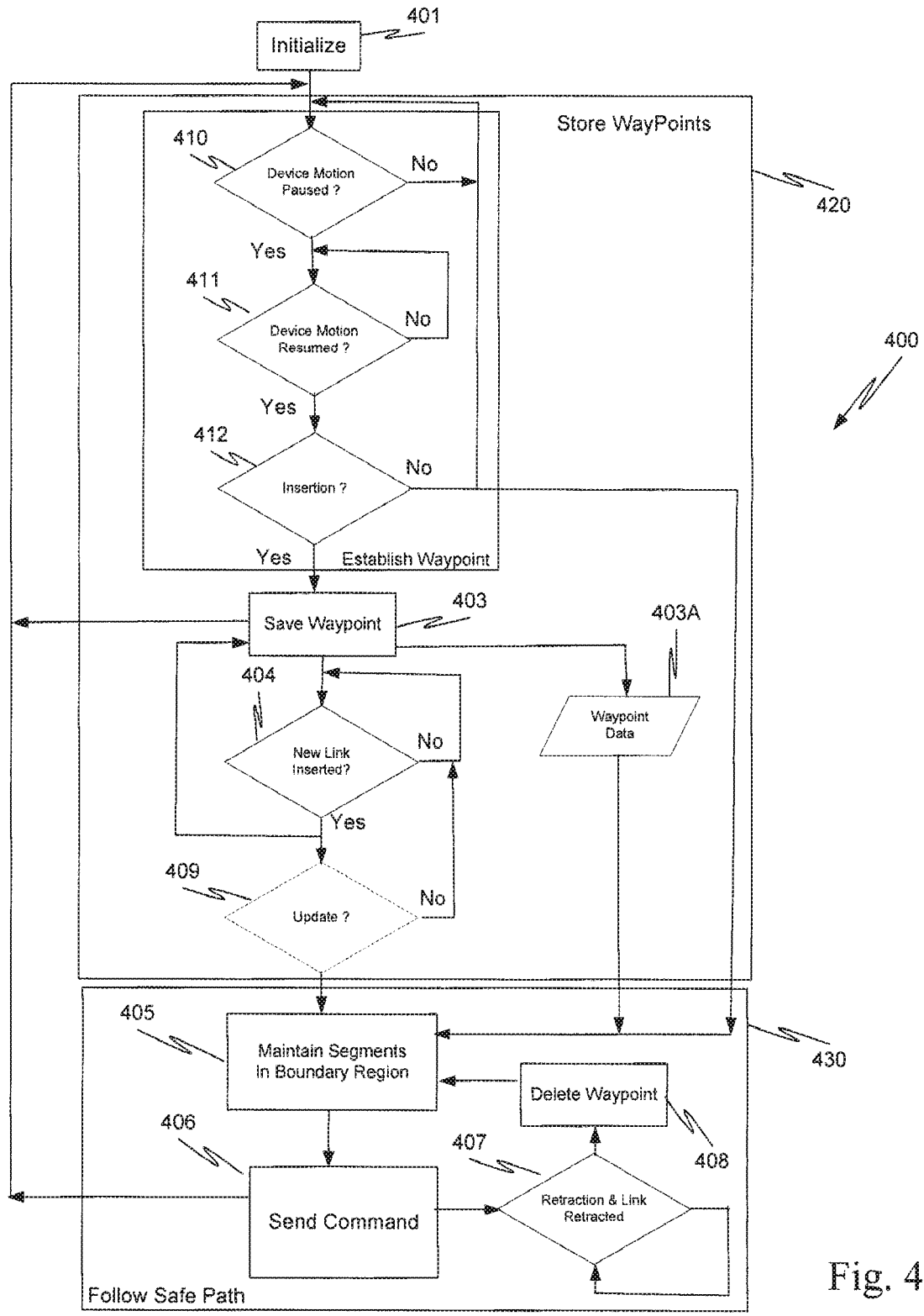
FIG. 4 is a process flow diagram for one embodiment of a method of configuring a steerable medical device to follow a safe path.

FIG. 4 is a process flow diagram for one embodiment of a method 400 used with a steerable medical device such as steerable endoscope 100. In one aspect, instructions in a METHOD 400 module 232 (FIG. 2) in memory 230 are executed on a processor in processor module 250 to perform at least some of the operations described more completely below.

In method 400, STORE WAYPOINTS operation 420, as described more completely below, saves waypoints of the tip of steerable endoscope 100 as an ordered sequence of locations. The ordered sequence of locations represents the trajectory of the tip as steerable endoscope 100 is inserted into the patient. As described above, the ordered sequence of locations defines a safe path 150 that has been selected by the operator of steerable endoscope 100.

The stored ordered sequence of locations is retrieved and analyzed in FOLLOW SAFE PATH process 430. FOLLOW SAFE PATH process 430 configures the articulatable portion of endoscope 100 so that the articulatable portion of endoscope 100 is constrained to follow safe path 150 as the articulatable portion moves within the patient. Herein, following the safe path does not mean that the safe path is followed exactly, but rather that the articulatable portion steerable endoscope 100 stays at least within a safe region, sometimes called a boundary region, about safe path 150.

In FIG. 4, one embodiment of STORE WAYPOINTS operation 420 and FOLLOW SAFE PATH process 430 are illustrated and described more completely below. This embodiment is illustrative only and is not intended to be limiting to the specific operations and processes described. In view of this disclosure, one knowledgeable in the field can utilize other techniques to move the articulatable portion of a steerable medical into and out of a patient while following the safe path described herein.

In FIG. 4, upon initiation of method 400, an INITIALIZE operation 401 is performed. INITIALIZE operation 401 initializes any variables, memory structures etc that are need for subsequent operations in method 400. In one aspect, INITIALIZE operation 401 uses display controller 235 (FIG. 2) to generate a display on display device 210 that permits the operator of steerable endoscope 100 to select parameters that define the extent of the boundary region, for example. Upon completion INITIALIZE operation 401 (FIG. 4) transfers processing to ESTABLISH WAYPOINT operation 402 in STORE WAYPOINTS operation 420.

In ESTABLISH WAYPOINT operation 402, a waypoint on the safe path of the endoscope is established. This can be done in a variety of ways. Accordingly, check operations 410 to 412, as discussed more completely below, are illustrative only and are not intended to be limiting to this particular implementation.

In one aspect, as the operator inserts steerable endoscope 100 into a body cavity (for instance, through an incision in the stomach into the abdominal cavity) insertion is paused periodically. When motion of endoscope 100 is paused, DEVICE MOTION PAUSED check operation 410 transfers processing to DEVICE MOTION RESUMED check operation 411.

If steerable endoscope 100 is paused to determine a safe trajectory for the tip, the operator uses the camera and illumination at the tip of steerable endoscope 100 to determine a safe trajectory inside the body cavity. When viewing the interior of the body cavity and determining a safe direction for farther insertion, the endoscope tip may be oriented in any direction to provide views of the body cavity.

Once a safe trajectory is determined, the tip is oriented in the direction that the operator intends steerable endoscope 100 to travel upon farther insertion. The operator then inserts endoscope 100 farther into the patient. However, the operator could also retract endoscope 100 after the pause. Thus, upon resumption of motion of endoscope 100, DEVICE MOTION RESUMED check operation 411 transfers processing to INSERTION check operation 412.

INSERTION check operation 412 determines whether after the pause, the operation is continuing to insert endoscope 100 or is retracting endoscope 100. If the operator is continuing to insert endoscope 100, check operation 412 transfers processing to SAVE WAYPOINT operation 403. Conversely, if the operator is retracting endoscope 100, check operation 412 transfers to DEVICE MOTION PAUSED check operation 410 and to MAINTAIN SEGMENTS IN BOUNDARY REGION operation 405.

Again, the combination of operations 410 to 412 is one way to allow an operator to establish a waypoint. Alternatively, the operator could, for example, push a button when a safe trajectory has been identified and the operator is about to move the endoscope tip on that trajectory.

Figure 2:
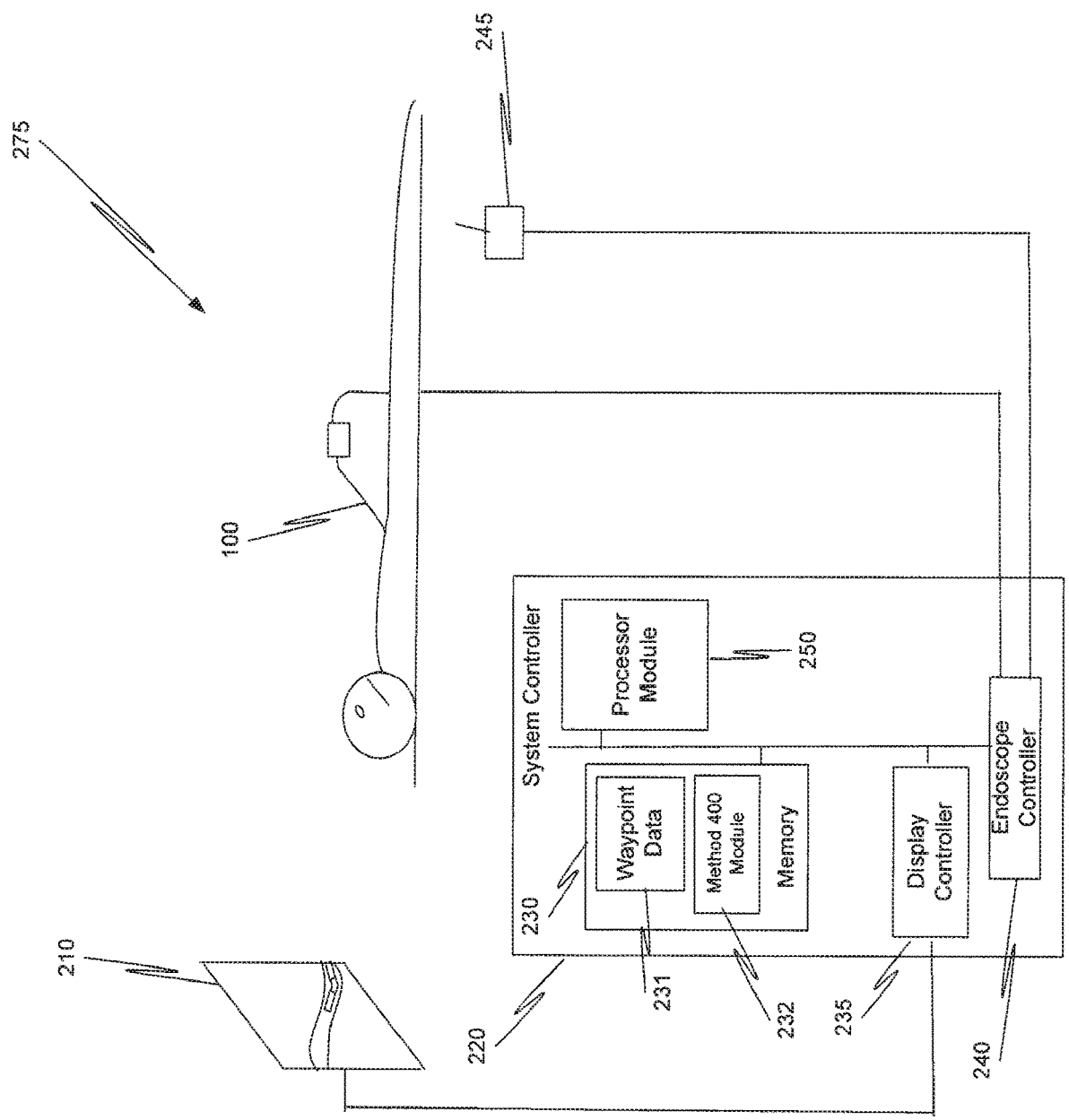
FIG. 2 is a diagrammatic view of an apparatus used in one aspect of the processes and operations described herein.

SAVE WAYPOINT operation 403 records the previous location of the tip as a waypoint in WAYPOINT DATA 403A, which in FIG. 2 is shown as waypoint data 231. SAVE WAYPOINT operation 403, upon completion, transfers processing to NEW LINK INSERTED check operation 404. SAVE WAYPOINT operation 403 also transfers back to the start of ESTABLISH WAYPOINT operation 402 in case the operator decides to change the direction of the safe trajectory.

In this example, insertion of a link is used as a trigger to record another waypoint for the tip. However, other criteria can be used so long as locations of the tip are saved with sufficient resolution to permit determining a safe path. As steerable endoscope 100 is moved further into the patient along the safe trajectory, as each new link is inserted in the patient, the location of the tip is saved as another waypoint. In this example, when a new link is inserted, NEW LINK INSERTED check operation 404 transfers processing to SAVE WAYPOINT operation 403, which was described above, and to UPDATE check operation 409.

UPDATE check operation 409 is shown with a dotted line in FIG. 4 because check operation 409 is optional. In one aspect, the configuration of the trailing segments of endoscope 100 is updated only after a predefined number of new waypoints have been saved. In this aspect, UPDATE check operation 409 does not transfer processing to process 405 until the predefined number of new waypoints is available in WAYPOINT DATA 403A. Also, UPDATE check operation 409 checks the states of the articulatable segments and if none of the articulatable segments have state articulating, UPDATE check operation 409 does not transfer processing to process 405. Alternatively, the configuration of the trailing segments of endoscope 100 is updated for each new waypoint and so UPDATE check operation 409 is not needed.

In this embodiment, FOLLOW SAFE PATH process 430 includes MAINTAIN SEGMENTS IN BOUNDARY REGION process 405 and SEND COMMAND process 406. MAINTAIN SEGMENTS IN BOUNDARY REGION process 405 uses the saved waypoints to generate a configuration for each of the inserted links so that trailing segments 101-1 to 101-3 follow safe path 150 of the tip as defined by the waypoints. As noted above, for some steerable medical devices, it may not be possible to configure the trailing segments to follow exactly safe path 150.

Thus, in one aspect, a boundary region about the ordered sequence of locations $\{P_k\}_{k=1}^{N}$ is generated. Here, $P_k$ denotes the Cartesian coordinates of the endoscope tip when the number of the inserted links is k. After the endoscope has been inserted for N links, the path trajectory of the endoscope tip is recorded as ordered sequence of locations $\{P_k\}_{k=1}^{N}$ in memory 230 (FIG. 2).

As described above, the boundary region defines a volume around safe path 150, i.e., a volume that encloses safe path 150. The trailing segments can safely pass through any part of the boundary region as the trailing segments move towards the surgical site, or move away from the surgical site.

Figure 5:
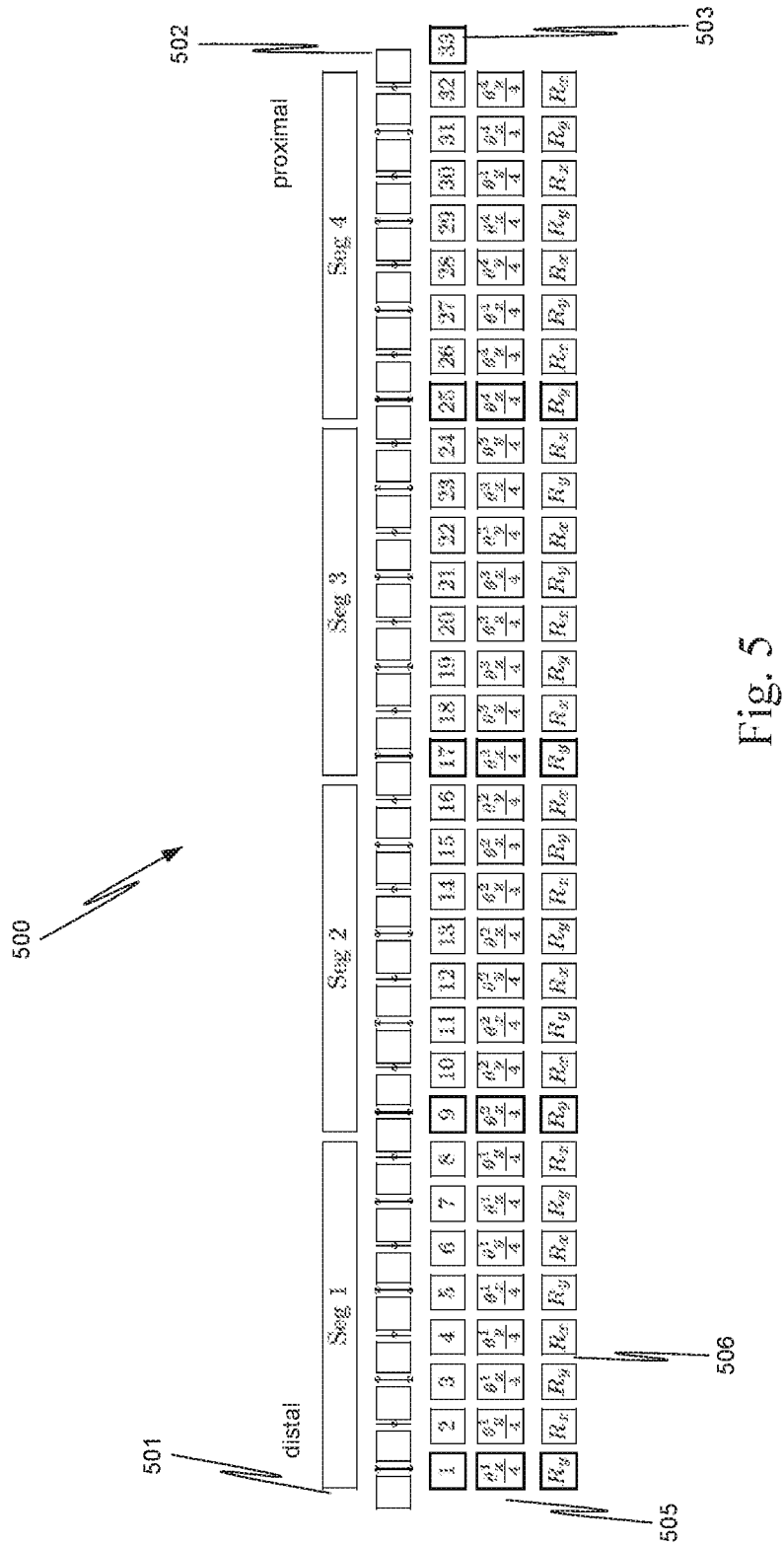
FIG. 5 is a diagrammatic view of elements of a kinematic model that can be used in the method of FIG. 4.

In one aspect, a kinematic model of steerable endoscope 100, such as model 500 in FIG. 5, is used in MAINTAIN SEGMENTS IN BOUNDARY REGION process 405. In kinematic model 500, (FIG. 5), a first level 501 of model 500 defines the number of articulatable segments in a plurality of articulatable segments of the steerable endoscope. In this example, the steerable endoscope has four articulatable segments Seg 1, Seg 2, Seg 3, and Seg 4.

A second level 502 of model 500 is a representation of links and joints in each of four articulatable segments Seg 1, Seg 2, Seg 3, and Seg 4. In this example, each segment includes eight links, where adjacent links are separated by a joint. The joints are numbered sequentially from the distal end to the proximal end of the endoscope, starting with a value one as shown in a third level 503 of model 500. (This numbering sequence is for convenience only. In other aspects, the numbering may increase in going from a proximal location towards a distal location.) Each link has a fixed length and the associated joint can rotate in a single plane, either the x-plane or the y-plane. The joints alternate so adjacent links rotate in different planes.

In model 500, each of four articulatable segments Seg 1, Seg 2, Seg 3, and Seg 4 has an angle of rotation about the x-axis and an angle of rotation about the y-axis. For articulatable segment Seg 1, the angle of rotation about the x-axis is $\theta_y^1$, (sometimes referred to as pitch) and the angle of rotation about the y-axis is $\theta_x^1$ (sometimes referred to as yaw). For articulatable segment Seg 2, the angle of rotation about the x-axis is $\theta_y^2$, and the angle of rotation about the y-axis is $\theta_x^2$. For articulatable segment Seg 3, the angle of rotation about the x-axis is $\theta_y^3$, and the angle of rotation about the y-axis is $\theta_x^3$. For articulatable segment Seg 4, the angle of rotation about the x-axis is $\theta_y^4$, and the angle of rotation about the y-axis is $\theta_x^4$.

Row 505 in model 500 gives the initial constraint on the joint angles. In this example, the joint angles for a segment are assumed to be equal. Thus, each joint angle is one-fourth of the corresponding segment angle. Row 506 in model 500 gives the roll matrix for each joint.

In this model, y-links are links that cause motion in the y-direction rather than links that rotate about the y-direction. This definition results in $R_x(\theta_y)$. Similarly, in this model, x-links are links that cause motion in the x-direction rather than links that rotate about the x-direction. This definition results in $R_y(\theta_x)$ Those knowledgeable in the field understand that alternative definitions can be used in the kinematic model, where x-links are links that rotate about the x-direction and y-links are links that rotate about the y-direction. Irrespective of the kinematic model definitions, the results are equivalent.

Thus, model 500 is illustrative only and is not intended to be limiting. Model 500 is used in one example that is developed more completely below.

Using stored ordered sequence of locations $\{P_k\}_{k=1}^N$ and kinematic model 500, a cost function is minimized to generate position and orientation data of the endoscope segments in MAINTAIN SEGMENTS IN BOUNDARY REGION process 405. Specifically, in one aspect, positions and orientations are generated for each of the links in the articulatable portion of endoscope 100. The positions and orientations are constrained within the boundary region.

The cost function allows the position and orientation to be optimized for a variety of criteria, for example, but not limited to: 1) maximum tip controllability; 2) maximum distance of the segments from inverse-kinematic singularities; 3) maximum distance of the segments from articulation limits; 4) maximum distance from user-defined body-cavity boundaries (organs, adhesions, etc.); 5) minimum distance from the defined path.

In process 405, the cost function may be a dynamically changing function of any number of criteria. However, the number of criteria is selected so the cost function can be minimized and the segments positioned to achieve the constrained movement within an endoscope movement time acceptable to the operator. Conventional techniques are used by a processor to minimize the cost function selected subject to the position constraints imposed.

In an additional aspect, an embodiment of process 405 determines the optimal configuration of the segments (relative segment angles) to satisfy the constraint that the segment links stay "near to" the path defined by the tip forward motion and any additional constraints on the link (or segment) positions.

For example, in process 405, the segments may be allowed to assume positions within a tubular bounding region 310A (FIG. 3A) around the tip path while encouraging tip manipulability. One way to encourage tip manipulability in process 405 is to minimize the sum of the absolute values of the relative joint angles, with the additional constraint that the link positions not deviate by more than a distance Δ at each of the waypoints in ordered sequence of locations $\{P_k\}_{k=1}^N$. In one aspect, distance Δ is specified by the operator.

Upon determining the configuration for each of the articulatable segments, MAINTAIN SEGMENTS IN BOUNDARY REGION process 405 transfers processing to SEND COMMAND process 406 (FIG. 4). In SEND COMMAND process 406, the processor in processor module 250 (FIG. 2) sends at least one command to the motors in endoscope controller 240 to configure the articulatable segments based on the locations and orientations generated in process 405, i.e., based on the configuration generated in process 405. This constrains the articulatable segments within the boundary region as endoscope 100 moves further into the patient.

SEND COMMAND process 406 transfers to DEVICE MOTION PAUSED check operation 410 and to RETRACTION AND LINK RETRACTED check operation 407. RETRACTION AND LINK RETRACTED check operation 407 determines whether endoscope 100 is being retracted and whether a link has been retracted. If both of these conditions are true, check operation 407 transfers to DELETE WAYPOINT operation 408.

DELETE WAYPOINT operation 408 deletes the stored waypoint for the withdrawn link and transfers to operation 405. Hence, operations 405 to 408 cause endoscope 100 to follow safe path 150 as endoscope 100 is retracted from the patient.

In the example of FIG. 2, in response to the command, endoscope controller 240 configures the segments so that as the segments move forward, the segments are constrained to stay within the boundary region. Thus, the segments may not follow the trajectory of the tip exactly, but the segments follow a path within the boundary region that is safe.

When the operator starts to withdraw the endoscope from the patient, the waypoints in the stored ordered sequence of locations $\{P_k\}_{k=1}^N$ decrease by one as each link is withdrawn. Processes 405 and 406 are used as steerable endoscope is withdrawn to maintain endoscope 100 with the boundary region.

As a further example of process 405, the control of the joint angles at constant endoscopic length increments is considered such that the endoscope configuration is kept within a safety area, the boundary region described above, during the process of insertion and withdrawal. In this example, a configuration of the trailing links that is closest, as measured by Euclidean norm, to the tip trajectory is generated in process 405, since the tip trajectory represents a safe route selected by the operator.

As described above $P_k$ denotes the Cartesian coordinate of the endoscope tip when the number of the inserted links is k. After the endoscope has been inserted for N links, the path trajectory of the endoscope tip is recorded in a series $\{P_k\}_{k=1}^N$. Process 405 controls the joint angles to achieve an endoscope link configuration close to the waypoints in recorded series $\{P_k\}_{k=1}^N$. This is formulated as the following optimization, where J is the cost function discussed above:

$$\min_\theta J = \frac{1}{2}\sum_{k=1}^{N}\|p_k - P_k\|^2 \qquad (1)$$

subject to $$\theta_{min} \le \theta \le \theta_{max}, \qquad (2)$$

where $p_k$ is the coordinate of each link determined by the kinematics model.

To apply an iterative procedure to solve this problem, assume that at the n-th step, a solution is $\theta_n$ and the next increment $\Delta\theta_n$ is to be determined. The new link coordinate is approximated by $$p^{n+1} \approx p^n + \nabla_{\theta_n} p \cdot \Delta\theta_n. \qquad (3)$$

Substituting expression (3) into the cost function gives:

$$J^{n+1} = 1/2\|p^{n+1} - P\|^2 \approx 1/2\|\nabla_{\theta_n}p \cdot \Delta\theta_n + p^n - P\|^2. \qquad (4)$$

This is indeed a quadratic programming problem:

$$\min_{\Delta\theta} J = \frac{1}{2}\Delta\theta_n (\nabla_{\theta_n} p)^T \nabla_{\theta_n} p \Delta\theta_n + (p^n - P)^T \nabla_{\theta_n} p \Delta\theta_n, \qquad (5)$$

subject to $$\theta_{min} - \theta_n \le \Delta\theta_n \le \theta_{max} - \theta_n. \qquad (6)$$

Kinematics Model

With respect to FIG. 5, let the first input parameter be defined as:

$$q = \begin{bmatrix} \theta_x^1 & \theta_y^1 \\ \theta_x^2 & \theta_y^2 \\ \theta_x^3 & \theta_y^3 \\ \theta_x^4 & \theta_y^4 \end{bmatrix}. \qquad (7)$$

The vector of joint angles is defined as:

$$q_{jw} = \left[ \frac{\theta_x^1}{4}, \frac{\theta_y^1}{4}, \frac{\theta_x^1}{4}, \frac{\theta_y^1}{4}, \frac{\theta_x^1}{4}, \frac{\theta_y^1}{4}, \frac{\theta_x^1}{4}, \frac{\theta_y^1}{4}, \frac{\theta_x^2}{4}, \right. \\ \frac{\theta_y^2}{4}, \frac{\theta_x^2}{4}, \frac{\theta_y^2}{4}, \frac{\theta_x^2}{4}, \frac{\theta_y^2}{4}, \frac{\theta_x^2}{4}, \frac{\theta_y^2}{4}, \frac{\theta_x^3}{4}, \frac{\theta_y^3}{4}, \frac{\theta_x^3}{4}, \frac{\theta_y^3}{4}, \frac{\theta_x^3}{4}, \\ \left. \frac{\theta_y^3}{4}, \frac{\theta_x^3}{4}, \frac{\theta_y^3}{4}, \frac{\theta_x^4}{4}, \frac{\theta_y^4}{4}, \frac{\theta_x^4}{4}, \frac{\theta_y^4}{4}, \frac{\theta_x^4}{4}, \frac{\theta_y^4}{4}, \frac{\theta_x^3}{4}, \frac{\theta_y^3}{4} \right], \qquad (8)$$

and the state of each link is defined as:

$$T_{lw}(1) = \begin{bmatrix} R_y\left(-\frac{\theta_x^1}{4}\right) & \begin{pmatrix} 0 \\ 0 \\ -a(1) \end{pmatrix} \\ 0 & 1 \end{bmatrix}, \qquad (9)$$

$$T_{lw}(3) = \begin{bmatrix} R_y\left(-\frac{\theta_x^1}{4}\right) & \begin{pmatrix} 0 \\ 0 \\ -a(3) \end{pmatrix} \\ 0 & 1 \end{bmatrix},$$

$$T_{lw}(5) = \begin{bmatrix} R_y\left(-\frac{\theta_x^1}{4}\right) & \begin{pmatrix} 0 \\ 0 \\ -a(5) \end{pmatrix} \\ 0 & 1 \end{bmatrix},$$

$$T_{lw}(7) = \begin{bmatrix} R_y\left(-\frac{\theta_x^1}{4}\right) & \begin{pmatrix} 0 \\ 0 \\ -a(7) \end{pmatrix} \\ 0 & 1 \end{bmatrix},$$

$$T_{lw}(2) = \begin{bmatrix} R_x\left(-\frac{\theta_y^1}{4}\right) & \begin{pmatrix} 0 \\ 0 \\ -a(2) \end{pmatrix} \\ 0 & 1 \end{bmatrix},$$

$$T_{lw}(4) = \begin{bmatrix} R_x\left(-\frac{\theta_y^1}{4}\right) & \begin{pmatrix} 0 \\ 0 \\ -a(4) \end{pmatrix} \\ 0 & 1 \end{bmatrix},$$

$$T_{lw}(6) = \begin{bmatrix} R_x\left(-\frac{\theta_y^1}{4}\right) & \begin{pmatrix} 0 \\ 0 \\ -a(6) \end{pmatrix} \\ 0 & 1 \end{bmatrix},$$

$$T_{lw}(8) = \begin{bmatrix} R_x\left(-\frac{\theta_y^1}{4}\right) & \begin{pmatrix} 0 \\ 0 \\ -a(8) \end{pmatrix} \\ 0 & 1 \end{bmatrix},$$

where $$R_x(\theta) = \begin{bmatrix} 1 & 0 & 0 \\ 0 & \cos(\theta) & -\sin(\theta) \\ 0 & \sin(\theta) & \cos(\theta) \end{bmatrix} \text{ and}$$

$$R_y(-\theta) = \begin{bmatrix} \cos(\theta) & 0 & -\sin(\theta) \\ 0 & 1 & 0 \\ \sin(\theta) & 0 & \cos(\theta) \end{bmatrix}$$

The rest of the $T_{lw}$'s can be obtained in a similar fashion. In particular, $$T_{lw}(33) = \begin{bmatrix} I & \begin{pmatrix} 0 \\ 0 \\ -a(33) \end{pmatrix} \\ 0 & 1 \end{bmatrix}. \qquad (10)$$

Notice that all these $T_{lw}$'s are in the Special Euclidean Lie group SE(4).

The cumulative transform to the base from the distal end of link k can be derived as $$T_{cl}(k) = \prod_{j=1}^{k} T_{lw}(j) = T_{lw}(1) \times T_{lw}(2) \times \ldots \times T_{lw}(k). \qquad (11)$$

In this section, gradient $\nabla_\theta l_k$ is derived, where l is the position vector for link k. To this end, define the basis for the skew-symmetric matrix so(3) as follows:

$$\sigma_x = \begin{bmatrix} 0 & 0 & 0 \\ 0 & 0 & -1 \\ 0 & 1 & 0 \end{bmatrix}, \sigma_y = \begin{bmatrix} 0 & 0 & 1 \\ 0 & 0 & 0 \\ -1 & 0 & 0 \end{bmatrix}, \quad (12)$$

$$\sigma_z = \begin{bmatrix} 0 & -1 & 0 \\ 1 & 0 & 0 \\ 0 & 0 & 0 \end{bmatrix}.$$

The rotation matrices can then be described as $$R_x(\theta) = \exp(\sigma_x \theta), R_y(\theta) = \exp(\sigma_y \theta), R_z(\theta) = \exp(\sigma_z \theta) \quad (13)$$

Suppose that R is a rotation matrix $$R = \begin{bmatrix} r_{11} & r_{12} & r_{13} \\ r_{21} & r_{22} & r_{23} \\ r_{31} & r_{32} & r_{33} \end{bmatrix}. \quad (14)$$

Since $RR^T = I$, an important property for R can be derived:

$$R\sigma_x R^T = r_{11}\sigma_x + r_{21}\sigma_y + r_{31}\sigma_z, \quad (15)$$

$$R^T \sigma_x R = r_{11}\sigma_x + r_{12}\sigma_y + r_{13}\sigma_z, \quad (16)$$

$$R\sigma_y R^T = r_{12}\sigma_x + r_{22}\sigma_y + r_{32}\sigma_z, \quad (17)$$

$$R^T \sigma_y R = r_{21}\sigma_x + r_{22}\sigma_y + r_{23}\sigma_z, \quad (18)$$

Now, the gradient $dT_{cl}(k)/d\theta$ is derived. Let $$T_{bw}(k) = \begin{bmatrix} R_k & a_k \\ 0 & 1 \end{bmatrix} \text{ and } T_{cl}(k) = \begin{bmatrix} S_k & l_k \\ 0 & 1 \end{bmatrix}. \quad (19)$$

It is easy to derive that $$S_k = R_1 R_2 \ldots R_k, \quad (20)$$

$$l_k = R_1 R_2 \ldots R_{k-1} a_k + R_1 R_2 \ldots R_{k-2} a_{k-1} + \ldots + R_1 a_2 + a_1 = S_{k-1} a_k + S_{k-2} a_{k-1} + \ldots + S_1 a_2 + a_1, \quad (21)$$

and $l_1 = a_1$. We therefore have $$\frac{dS_k}{d\theta} = \frac{d}{d\theta}(R_1 R_2 \ldots R_k), \quad (22)$$

$$\frac{dl_k}{d\theta} = \frac{dS_{k-1}}{d\theta} a_k + \frac{dS_{k-2}}{d\theta} a_{k-1} + \ldots + \frac{dS_1}{d\theta} a_2, \; (k \geq 2). \quad (23)$$

When $\theta = \theta_x^1$, for $k \geq 7$, we have $$\frac{dS_k}{d\theta_x^1} S_k^T = \frac{d}{d\theta_x^1}(R_1 R_2 \ldots R_k) S_k^T \quad (24)$$

$$= \frac{dR_1}{d\theta_x^1}(R_2 \ldots R_k) S_k^T + R_1 R_2 \frac{dR_3}{d\theta_x^1}(R_4 \ldots R_k) S_k^T +$$

$$R_1 R_2 R_3 R_4 \frac{dR_5}{d\theta_x^1}(R_6 \ldots R_k) S_k^T +$$

$$R_1 R_2 R_3 R_4 R_5 R_6 \frac{dR_7}{d\theta_x^1}(R_8 \ldots R_k) S_k^T$$

$$= \left(-\frac{\sigma_y}{4}\right) + R_1 R_2 \left(-\frac{\sigma_y}{4}\right)(R_1 R_2)^T + \quad (25)$$

$$R_1 R_2 R_3 R_4 \left(-\frac{\sigma_y}{4}\right)(R_1 R_2 R_3 R_4)^T +$$

$$R_1 R_2 R_3 R_4 R_5 R_6 \left(-\frac{\sigma_y}{4}\right)(R_1 R_2 R_3 R_4 R_5 R_6)^T$$

$$= -\frac{\sigma_y}{4} + S_2 \left(-\frac{\sigma_y}{4}\right) S_2^T + S_4 \left(-\frac{\sigma_y}{4}\right) S_4^T + S_6 \left(-\frac{\sigma_y}{4}\right) S_6^T, \quad (26)$$

which in turn yields $$\frac{dS_k}{d\theta_x^1} = -\frac{1}{4}(\sigma_y + S_2 \sigma_y S_2^T + S_4 \sigma_y S_4^T + S_6 \sigma_y S_6^T) S_k. \quad (27)$$

For k=5 or 6, we obtain $$\frac{dS_k}{d\theta_x^1} S_k^T = -\frac{\sigma_y}{4} + S_2\left(-\frac{\sigma_y}{4}\right) S_2^T + S_4\left(-\frac{\sigma_y}{4}\right) S_4^T, \quad (28)$$

thus $$\frac{dS_k}{d\theta_x^1} = -\frac{1}{4}(\sigma_y + S_2 \sigma_y S_2^T + S_4 \sigma_y S_4^T) S_k;$$

for k=3 or 4, $$\frac{dS_k}{d\theta_x^1} = -\frac{1}{4}(\sigma_y + S_2 \sigma_y S_2^T) S_k; \quad (29)$$

and for k=1 or 2, $$\frac{dS_k}{d\theta_x^1} = -\frac{1}{4} \sigma_y S_k; \quad (30)$$

In summary, $$\frac{dS_k}{d\theta_x^1} = \begin{cases} -\frac{1}{4}\sigma_y S_k, & k = 1, 2; \\ -\frac{1}{4}(\sigma_y + S_2 \sigma_y S_2^T) S_k, & k = 3, 4; \\ -\frac{1}{4}(\sigma_y + S_2 \sigma_y S_2^T + S_4 \sigma_y S_4^T) S_k, & k = 5, 6; \\ -\frac{1}{4}(\sigma_y + S_2 \sigma_y S_2^T + S_4 \sigma_y S_4^T + S_6 \sigma_y S_6^T) S_k, & k \geq 7. \end{cases} \quad (31)$$

$$\frac{dS_k}{d\theta_x^2} = \quad (32)$$

$$\begin{cases} 0, & k \leq 8; \\ -\frac{1}{4}(S_8 \sigma_y S_8^T) S_k, & k = 9, 10; \\ -\frac{1}{4}(S_8 \sigma_y S_8^T + S_{10} \sigma_y S_{10}^T) S_k, & k = 11, 12; \\ -\frac{1}{4}(S_8 \sigma_y S_8^T + S_{10} \sigma_y S_{10}^T + S_{12} \sigma_y S_{12}^T) S_k, & k = 13, 14; \\ -\frac{1}{4}(S_8 \sigma_y S_8^T + S_{10} \sigma_y S_{10}^T + S_{12} \sigma_y S_{12}^T + S_{14} \sigma_y S_{14}^T) S_k, & k \geq 15. \end{cases}$$

-continued $$\frac{dS_k}{d\theta_x^3} = $$  (33)

$$\begin{cases} 0, & k \le 16; \\ -\frac{1}{4}(S_{16}\sigma_y S_{16}^T)S_k, & k = 17, 18; \\ -\frac{1}{4}(S_{16}\sigma_y S_{16}^T + S_{18}\sigma_y S_{18}^T)S_k, & k = 19, 20; \\ -\frac{1}{4}(S_{16}\sigma_y S_{16}^T + S_{18}\sigma_y S_{18}^T + S_{20}\sigma_y S_{20}^T)S_k, & k = 21, 22; \\ -\frac{1}{4}(S_{16}\sigma_y S_{16}^T + S_{18}\sigma_y S_{18}^T + S_{20}\sigma_y S_{20}^T + S_{22}\sigma_y S_{22}^T)S_k, & k \ge 23. \end{cases}$$

Similarly, $$\frac{dS_k}{d\theta_y^1} = \begin{cases} 0, & k = 1; \\ \frac{1}{4}(S_1\sigma_x S_1^T)S_k, & k = 2, 3; \\ \frac{1}{4}(S_1\sigma_x S_1^T + S_3\sigma_x S_3^T)S_k, & k = 4, 5; \\ \frac{1}{4}(S_1\sigma_x S_1^T + S_3\sigma_x S_3^T + S_5\sigma_x S_5^T)S_k, & k = 6, 7; \\ \frac{1}{4}(S_1\sigma_x S_1^T + S_3\sigma_x S_3^T + S_5\sigma_x S_5^T + S_7\sigma_x S_7^T)S_k, & k \ge 8. \end{cases}$$  (34)

$$\frac{dS_k}{d\theta_y^2} = $$  (35)

$$\begin{cases} 0, & k = 9; \\ \frac{1}{4}(S_9\sigma_x S_9^T)S_k, & k = 10, 11; \\ \frac{1}{4}(S_9\sigma_x S_9^T + S_{11}\sigma_x S_{11}^T)S_k, & k = 12, 13; \\ \frac{1}{4}(S_9\sigma_x S_9^T + S_{11}\sigma_x S_{11}^T + S_{13}\sigma_x S_{13}^T)S_k, & k = 14, 15; \\ \frac{1}{4}(S_9\sigma_x S_9^T + S_{11}\sigma_x S_{11}^T + S_{13}\sigma_x S_{13}^T + S_{15}\sigma_x S_{15}^T)S_k, & k \ge 16. \end{cases}$$

$$\frac{dS_k}{d\theta_y^3} = $$  (36)

$$\begin{cases} 0, & k = 17; \\ \frac{1}{4}(S_{17}\sigma_x S_{17}^T)S_k, & k = 18, 19; \\ \frac{1}{4}(S_{17}\sigma_x S_{17}^T + S_{19}\sigma_x S_{19}^T)S_k, & k = 20, 21; \\ \frac{1}{4}(S_{17}\sigma_x S_{17}^T + S_{19}\sigma_x S_{19}^T + S_{21}\sigma_x S_{21}^T)S_k, & k = 22, 23; \\ \frac{1}{4}(S_{17}\sigma_x S_{17}^T + S_{19}\sigma_x S_{19}^T + S_{21}\sigma_x S_{21}^T + S_{23}\sigma_x S_{23}^T)S_k, & k \ge 24. \end{cases}$$

In this subsection, the Jacobian is derived. Let $$T_J(k) = \prod_{j=k+1}^{N} T_{lw}(j) = T_{lw}(k+1) \times \ldots \times T_{lw}(N).$$  (37)

and denote its blocks as $$T_J(k) = \begin{bmatrix} R_k^J & l_k^J \\ 0 & 1 \end{bmatrix}.$$  (38)

Recalling Eq. (19), we have $$\frac{dT_{cl}(N)}{d\theta_x^1} = \begin{bmatrix} \frac{dS_N}{d\theta_x^1} & \frac{dl_N}{d\theta_x^1} \\ 0 & 0 \end{bmatrix}$$  (39)

$$= \frac{dT_{lw}(1)}{d\theta_x^1} T_{lw}(2) \ldots T_{lw}(N) +$$

$$T_{lw}(1) T_{lw}(2) \frac{dT_{lw}(3)}{d\theta_x^1} T_{lw}(4) \ldots T_{lw}(N) +$$

$$T_{lw}(1) T_{lw}(2) T_{lw}(3) T_{lw}(4) \frac{dT_{lw}(5)}{d\theta_x^1} T_{lw}(6) \ldots T_{lw}(N) +$$

$$T_{lw}(1) T_{lw}(2) T_{lw}(3) T_{lw}(4) T_{lw}(5) T_{lw}(6) \frac{dT_{lw}(7)}{d\theta_x^1} T_{lw}(8) \ldots$$

$$T_{lw}(N)$$

$$= \begin{bmatrix} -R_1 \frac{\sigma_y}{4} & 0 \\ 0 & 0 \end{bmatrix} T_J(1) + T_{cl}(2) \begin{bmatrix} -R_3 \frac{\sigma_y}{4} & 0 \\ 0 & 0 \end{bmatrix} T_J(3) +$$

$$T_{cl}(4) \begin{bmatrix} -R_5 \frac{\sigma_y}{4} & 0 \\ 0 & 0 \end{bmatrix} T_J(5) + T_{cl}(6) \begin{bmatrix} -R_7 \frac{\sigma_y}{4} & 0 \\ 0 & 0 \end{bmatrix} T_J(7).$$

The last equality is obtained by the definition of $T_{cl}$ and $T_J$. Proceeding further, we have $$\frac{dT_{cl}(N)}{d\theta_x^1} = \begin{bmatrix} -R_1 \frac{\sigma_y}{4} & 0 \\ 0 & 0 \end{bmatrix} \begin{bmatrix} R_1^J & l_1^J \\ 0 & 1 \end{bmatrix} + \begin{bmatrix} S_2 & l_2 \\ 0 & 1 \end{bmatrix} \begin{bmatrix} -R_3 \frac{\sigma_y}{4} & 0 \\ 0 & 0 \end{bmatrix} \begin{bmatrix} R_3^J & l_3^J \\ 0 & 1 \end{bmatrix} +$$

$$\begin{bmatrix} S_4 & l_4 \\ 0 & 1 \end{bmatrix} \begin{bmatrix} -R_5 \frac{\sigma_y}{4} & 0 \\ 0 & 0 \end{bmatrix} \begin{bmatrix} R_5^J & l_5^J \\ 0 & 1 \end{bmatrix} + \begin{bmatrix} S_6 & l_6 \\ 0 & 1 \end{bmatrix} \begin{bmatrix} -R_7 \frac{\sigma_y}{4} & 0 \\ 0 & 0 \end{bmatrix} \begin{bmatrix} R_7^J & l_7^J \\ 0 & 1 \end{bmatrix}$$

$$= \begin{bmatrix} -S_1 \frac{\sigma_y}{4} R_1^J - S_3 \frac{\sigma_y}{4} R_3^J - S_5 \frac{\sigma_y}{4} R_5^J - S_7 \frac{\sigma_y}{4} R_7^J \\ 0 \\ -S_1 \frac{\sigma_y}{4} l_1^J - S_3 \frac{\sigma_y}{4} l_3^J - S_5 \frac{\sigma_y}{4} l_5^J - S_7 \frac{\sigma_y}{4} l_7^J \\ 0 \end{bmatrix}$$

Therefore, the derivative of the position vector $l_N$ with respect to the joint angle $\theta_x^1$ is $$\frac{dl_N}{d\theta_x^1} = -S_1 \frac{\sigma_y}{4} l_1^J - S_3 \frac{\sigma_y}{4} l_3^J - S_5 \frac{\sigma_y}{4} l_5^J - S_7 \frac{\sigma_y}{4} l_7^J$$  (40)

$$= \frac{S_1}{4} \begin{bmatrix} -l_{1,3}^J \\ 0 \\ l_{1,1}^J \end{bmatrix} + \frac{S_3}{4} \begin{bmatrix} -l_{3,3}^J \\ 0 \\ l_{3,1}^J \end{bmatrix} + \frac{S_5}{4} \begin{bmatrix} -l_{5,3}^J \\ 0 \\ l_{5,1}^J \end{bmatrix} + \frac{S_7}{4} \begin{bmatrix} -l_{7,3}^J \\ 0 \\ l_{7,1}^J \end{bmatrix}.$$

In the above examples, the sequence of ordered locations and six-degrees of freedom were considered in configuring articulatable segments to remain within a boundary region, sometimes called a safe region. However, in some applications, consideration of only two-degrees of freedom may be sufficient. The x-y position could be controlled, or the pitch and the yaw could be controlled. In these applications, each waypoint only includes two degrees of freedom corresponding to an insertion depth and the above processes become less computationally intensive while the safe path is followed.

System controller 220 (FIG. 2) is illustrated as unified structures for ease of illustration and understanding. This is illustrative only and is not intended to be limiting. The various component of system controller 220 can be located apart and still perform the functions described.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

While the memory in FIG. 2 is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A system comprising:
   a controller configured to:
   store a first waypoint corresponding to a first position of a tip of a steerable medical device, the steerable medical device including an articulatable segment;
   perform a motion pause check operation to determine that an insertion motion of the articulatable segment into a patient anatomy has been paused, wherein the tip of the steerable medical device is at a second position when the insertion motion of the articulatable segment is paused;
   while the insertion motion of the articulatable segment is paused, receive control instructions to orient a tip of the steerable medical device from a first orientation toward a second orientation, wherein the second orientation indicates a safe traversal trajectory for farther insertion through the patient anatomy;
   determine that the articulatable segment has resumed the insertion motion into the patient anatomy;
   after determining that the articulatable segment has resumed the insertion motion, store a second waypoint corresponding to the second position of the tip of the steerable medical device;
   define a boundary region, the boundary region forming a three-dimensional volume enclosing the stored waypoints; and
   constrain the articulatable segment to remain within the boundary region as the articulatable segment is inserted in the patient anatomy, wherein the constraining of the articulatable segment is initiated based on a determination that a predetermined number of waypoints have been stored, wherein the predetermined number of waypoints includes a plurality of waypoints.

2. The system of claim 1, wherein the first and second waypoints are disposed along a first trajectory.

3. The system of claim 1, wherein the controller is further configured to:
   while the insertion motion of the articulatable segment is paused, receive one or more camera views of the patient anatomy to determine the second orientation.

4. The system of claim 1, wherein the controller is further configured to:
   perform a second motion pause check operation to determine that the insertion motion of the articulatable segment into the patient anatomy has been paused, wherein the tip of a steerable medical device is at a third position when the insertion motion of the articulatable segment is paused;
   determine that the articulatable segment has resumed the insertion motion into the patient anatomy; and
   after determining that the articulatable segment has resumed the insertion motion, store a third waypoint corresponding to the third position of the tip of the steerable medical device,
   wherein the three-dimensional volume encloses the stored waypoints, including the first, second, and third waypoints.

5. The system of claim 1, wherein the articulatable segment includes a plurality of sequentially arranged sections.

6. The system of claim 5, wherein a first section of the plurality of sequentially arranged sections is positioned within a patient anatomy when the first waypoint is stored.

7. The system of claim 6, wherein the controller is further configured to:
   determine an insertion of a second section of the plurality of sequentially arranged sections into the patient anatomy, wherein the second section is proximally adjacent to the first section in the plurality of sequentially arranged sections; and
   based on the determined insertion of the second section, trigger storage of a third waypoint corresponding to a third position of the tip of the steerable medical device.

8. The system of claim 1, wherein a cross-sectional shape of the boundary region varies along a length of the boundary region.

9. The system of claim 8, wherein the cross-sectional shape of the boundary region is determined based on a type of medical procedure to be performed.

10. The system of claim 8, wherein the cross-sectional shape of the boundary region is determined based on a type of the steerable medical device.

11. A system comprising:
    a controller configured to:
    store a first waypoint corresponding to a first three-dimensional position of a tip of a steerable medical device in a fixed reference frame, the steerable medical device including an articulatable segment, the articulatable segment including a plurality of sequentially arranged sections, wherein a first section of the plurality of sequentially arranged sections is positioned within a patient anatomy when the first waypoint is stored;
    perform a motion pause check operation to determine that a motion of the steerable medical device has been paused;

while the insertion motion of the articulatable segment is paused, receive control instructions to orient the tip of the steerable medical device from a first orientation toward a second orientation, wherein the second orientation indicates a safe traversal trajectory for farther insertion through a patient anatomy;

determine an insertion of a second section of the plurality of sequentially arranged sections into the patient anatomy along the safe traversal trajectory, wherein the second section is proximally adjacent to the first section in the plurality of sequentially arranged sections;

based on the determined insertion of the second section, trigger storage of a second waypoint corresponding to a second three-dimensional position of the tip of the steerable medical device in the fixed reference frame;

define a boundary region, the boundary region forming a three-dimensional volume enclosing the stored waypoints; and constrain the articulatable segment to remain within the boundary region while one or more of the plurality of sequentially arranged sections deviate from a path determined using the stored waypoints as the articulatable segment is inserted in the patient anatomy, wherein the constraining of the articulatable segment is initiated based on a determination that a predetermined number of waypoints have been stored, wherein the predetermined number of waypoints includes a plurality of waypoints.

12. The system of claim 11, wherein the controller is further configured to:

determine an insertion of a third section of the plurality of sequentially arranged sections into a patient anatomy, wherein the third section is proximally adjacent to the second section in the plurality of sequentially arranged sections; and based on the determined insertion of the third section, trigger storage of a third waypoint corresponding to a third three-dimensional position of the tip of the steerable medical device in the fixed reference frame, wherein the boundary region forms a three-dimensional volume enclosing the stored waypoints, including the third waypoint.

13. The system of claim 11, wherein the controller is further configured to:

while the steerable medical device is paused, receive one or more camera views of the patient anatomy to determine the second orientation.

14. The system of claim 11, wherein the controller is further configured to:

perform a motion resumed check operation to determine that a resumed motion of the steerable medical device is in an insertion direction along the safe traversal trajectory; and based on the determination that the resumed motion is in an insertion direction, initiate the storing of the first waypoint.

15. The system of claim 14, wherein the first and second waypoints are disposed along the safe traversal trajectory.

16. The system of claim 11, wherein the controller is further configured to:

determine a movement of the steerable medical device in a retraction direction.

17. The system of claim 11, wherein a cross-sectional shape of the boundary region varies along a length of the boundary region.

18. The system of claim 17, wherein the cross-sectional shape of the boundary region is determined based on a type of medical procedure to be performed.

* * * * *